(12) United States Patent
Nava et al.

(10) Patent No.: US 10,570,107 B2
(45) Date of Patent: *Feb. 25, 2020

(54) VINYL-CONTAINING COMPOUNDS AND PROCESSES FOR MAKING THE SAME

(71) Applicant: Reichhold LLC 2, Durham, NC (US)

(72) Inventors: Hildeberto Nava, Cary, NC (US); Yongning Liu, Apex, NC (US)

(73) Assignee: Reichhold LLC 2, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/941,586

(22) Filed: Mar. 30, 2018

(65) Prior Publication Data

US 2018/0290992 A1  Oct. 11, 2018

Related U.S. Application Data

(63) Continuation of application No. 15/233,318, filed on Aug. 10, 2016, now Pat. No. 9,957,243, which is a continuation of application No. 13/024,547, filed on Feb. 10, 2011, now abandoned.

(60) Provisional application No. 61/307,486, filed on Feb. 24, 2010.

(51) Int. Cl.
| | |
|---|---|
| *C07D 301/00* | (2006.01) |
| *C08G 63/47* | (2006.01) |
| *C08G 63/91* | (2006.01) |
| *C07C 67/08* | (2006.01) |
| *C07C 67/30* | (2006.01) |

(52) U.S. Cl.
CPC ............ *C07D 301/00* (2013.01); *C07C 67/08* (2013.01); *C07C 67/30* (2013.01); *C08G 63/47* (2013.01); *C08G 63/914* (2013.01)

(58) Field of Classification Search
CPC ....... C07D 301/00; C07C 67/30; C07C 67/08; C08G 63/47; C08G 63/914
See application file for complete search history.

(56) References Cited

U.S. PATENT DOCUMENTS

| | | |
|---|---|---|
| 3,367,992 A | 2/1968 | Bearden |
| 3,804,735 A | 4/1974 | Radlove et al. |
| 3,836,600 A | 9/1974 | Brewbaker et al. |
| 3,893,829 A | 7/1975 | Valentino |
| 3,947,422 A | 3/1976 | Tatum et al. |
| 3,948,698 A | 4/1976 | Elrick et al. |
| 4,014,771 A | 3/1977 | Rosenkranz et al. |
| 4,119,609 A | 10/1978 | Allen et al. |
| 4,134,884 A | 1/1979 | Takiyama et al. |
| 4,141,883 A | 2/1979 | Soma et al. |
| 4,310,708 A | 1/1982 | Strege et al. |
| 4,324,717 A | 4/1982 | Layer |
| 4,393,830 A | 7/1983 | Bodine |
| 4,546,142 A | 10/1985 | Walewski |
| 4,665,137 A | 5/1987 | Percec |
| 4,701,514 A | 10/1987 | Percec |
| 4,806,601 A | 2/1989 | Percec |
| 5,096,938 A | 3/1992 | Beck et al. |
| 5,118,783 A | 6/1992 | Raju |
| 5,373,058 A | 12/1994 | Hager et al. |
| 5,492,668 A | 2/1996 | Smeal et al. |
| 5,501,830 A | 3/1996 | Smeal et al. |
| 5,728,872 A | 3/1998 | Riemenschneider |
| 5,747,607 A | 5/1998 | Hager et al. |
| 5,821,383 A | 10/1998 | Haussling et al. |
| 5,874,503 A | 2/1999 | Scheibelhoffer et al. |
| 6,063,957 A | 5/2000 | Koniger et al. |
| 6,107,362 A | 8/2000 | Koniger et al. |
| 6,107,446 A | 8/2000 | Loza et al. |
| 6,150,458 A | 11/2000 | Weikard et al. |
| 6,153,788 A | 11/2000 | Fischer et al. |
| 6,187,442 B1 | 2/2001 | Lane et al. |
| 6,200,460 B1 | 3/2001 | Sutoris et al. |
| 6,228,688 B1 | 5/2001 | Ohta et al. |
| 6,268,467 B1 | 7/2001 | Lai et al. |
| 6,458,991 B1 | 10/2002 | Paulus et al. |
| 6,468,662 B1 | 10/2002 | Nava |
| 6,835,786 B2 | 12/2004 | Ishii et al. |
| 7,388,057 B2 | 6/2008 | Amagai et al. |
| 7,781,537 B2 | 8/2010 | Birsak et al. |
| 8,039,559 B2 | 10/2011 | Jansen et al. |

(Continued)

FOREIGN PATENT DOCUMENTS

| | | |
|---|---|---|
| EP | 0054105 | 6/1982 |
| EP | 0126341 | 4/1984 |

(Continued)

OTHER PUBLICATIONS

Fisher 1, Isooctane Material Safety Data Sheet, pp. 1-8, Jun. 22, 2009.
Fisher 2, Cyclohexane Material Safety Data Sheet, pp. 1-8, Oct. 6, 2009.
International Preliminary Report on Patentability for PCT/US2011/024970 dated Sep. 7, 2012.

(Continued)

*Primary Examiner* — Robert S Jones
(74) *Attorney, Agent, or Firm* — Neal, Gerber & Eisenberg LLP (57) ABSTRACT

The present invention provides a process for forming vinyl-containing compounds including the steps of: a) reacting in a nitrogen atmosphere a dicarboxylic acid and/or anhydride and a functional mono or polyfunctional alcohol to provide a hydroxyl-containing polyester; b) reacting the hydroxyl-containing polyester with a vinyl-containing organic acid in the presence of an esterification catalyst, a polymerization inhibitor and an azeotropic agent; and c) reacting the vinyl functional esterified intermediate, residual esterification catalyst and residual vinyl-containing organic acid with an epoxy to provide the vinyl-containing compound.

16 Claims, 3 Drawing Sheets

(56) References Cited

U.S. PATENT DOCUMENTS

| | | |
|---|---|---|
| 2004/0068088 A1 | 4/2004 | Loza et al. |
| 2004/0076830 A1 | 4/2004 | Riley et al. |
| 2005/0277745 A1 | 12/2005 | Walrath et al. |
| 2007/0179250 A1 | 8/2007 | Chen et al. |
| 2009/0022998 A1 | 1/2009 | Toth et al. |
| 2009/0076218 A1 | 3/2009 | Zhao et al. |
| 2009/0197094 A1 | 8/2009 | Nakahra et al. |
| 2011/0172359 A1 | 7/2011 | Panther |
| 2011/0207950 A1 | 8/2011 | Nava et al. |

FOREIGN PATENT DOCUMENTS

| | | |
|---|---|---|
| WO | WO1990012824 | 11/1990 |
| WO | WO2001040149 | 6/2001 |
| WO | WO2001040404 | 6/2001 |
| WO | WO2001042313 | 6/2001 |
| WO | WO2003093384 | 11/2003 |
| WO | WO2008119973 | 10/2008 |

OTHER PUBLICATIONS

International Preliminary Report on Patentability for PCT/US2013/073027 dated Jul. 2, 2015.
International Search Report and Written Opinion for PCT/US2011/024970 dated Jun. 7, 2011.
International Search Report and Written Opinion for PCT/US2013/073027 dated Mar. 27, 2014.
Linde, White Paper: Gas applications in fine and specialty chemistry, pp. 10-11, Apr. 4, 2008.
Reinhardt, "Inerting in the chemical industry," Hydrocarbon Processing, pp. 1-16, Apr. 2010.

Figure 1. Viscosity stability of Example 6 resin at RT and 65°C for 60 days

Figure 2. MW Stability of Example 6 resin at RT and 65°C for 60 days

Figure 3. Color Stability of Example 6 resin at RT and 65°C for 60 days

VINYL-CONTAINING COMPOUNDS AND PROCESSES FOR MAKING THE SAME

CROSS-REFERENCE TO RELATED APPLICATIONS

This application is a continuation of U.S. patent application Ser. No. 15/233,318, filed on Aug. 10, 2016, which is a continuation of U.S. patent application Ser. No. 13/024,547, filed on Feb. 10, 2011, which claims priority to U.S. Provisional App. No. 61/307,486, filed on Feb. 24, 2010, the disclosures of which are hereby incorporated by reference in their entirety.

FIELD OF THE INVENTION

The present invention generally relates to processes for preparing compounds having vinyl functionality.

BACKGROUND OF THE INVENTION

Reduction of styrene emissions remains a key issue in open mold processes using styrene-containing materials such as unsaturated polyesters, vinyl esters and other thermosetting resins. One of the largest areas of applications is the open mold process, particularly hand lay-up, spray-up, non-reinforced castings, gelcoats, filament winding and the like. New environmental concerns; however, demand better control on the emissions of organic compounds into the environment. This is prompting the polymer industry to find ways to develop technologies that can provide less potential hazards to workers in contact with the thermosetting resins. At the same time, the market requires that the new products should have minimal increase in cost when commercialized and do not compromise reactivity of the resins. Important is that all materials should also have good compatibility with all components in the mixtures. Viscosities should stay within an acceptable range so that pouring or spraying is not compromised. Wetting of glass or fillers also need to be maintained and physical properties should be similar or better than the standard materials currently being used.

Several methods have been proposed as possible ways to reduce styrene to minimize monomer emissions during the curing process of unsaturated polyesters or vinyl esters. One common method is the replacement of styrene by another reactive diluent that can produce fewer emissions during curing. This approach can lead to systems with slower reactivity, incomplete curing and higher costs. Reducing the amount of styrene or reactive diluent has been used as an attempt to reduce emissions. However, this approach leads to higher viscosities, making more difficult for hand-lay-up, rolling or spraying of the resins.

Another approach involves the preparation of low molecular weight polymers. Polymers with lower molecular weight are more soluble in styrene or other reactive diluent yielding lower viscosities and therefore requiring lower amount of diluents. Problems associated with lower molecular weight thermosetting systems are that the resulting physical properties of the final products are often compromised. Overall, products typically have inferior performance comparing to those of higher molecular weight components.

Another common approach also used in the reduction of styrene emissions is adding waxes to the thermosetting resins. Waxes limit the elimination of diluent vapors during the curing, however, one of the problems encountered with this approach is that there is poor interlaminate bonding.

The esterification of hydroxyl containing polycondensates with unsaturated carboxylic acids have become increasingly interesting commercially as coating resins and other coating materials, owing to their being solvent free and having easy processability. These esters are (meth)acrylic acid esters which are based on polyhydric alcohols and oligoesters formed from polyhydric alcohols reacted with polyfunctional acids or anhydrides. Their area of application is mainly in coating compositions curable by UV or electron beam. One preferred method of preparing (meth)acrylates is the direct esterification of the polyhydric aligo-alcohols with acrylic or methacrylic acid in the presence of esterification catalyst and of a solvent which forms and azeotropic mixture with water entraining agent. Typical reaction temperatures can range from 90° C. to 150° C. High reaction temperatures require a large amount of inhibitors in order to achieve good yields of the esterification products and for effectively suppressing the polymerization of (meth)acrylic acid esters. In addition to adding inhibitor, a stream of air needs to be added to maintain the inhibitors active and prevent polymerization of the (meth)acrylate intermediates. The polymerization inhibitors in combination with air and high temperatures generate a strong color in the reaction mixture, therefore making difficult to prepare materials with low color. The dark end products need to be washed with color scavenging compounds, which is time consuming, reduces the ester yield, increases the requirement of solvents as water containing agent, which have to be distilled again, and moreover leads to a high level of pollution and waste water.

Exemplary prior art references include U.S. Pat. Nos. 5,874,503 and 4,546,142 and describe the use of waxes with a variety of unsaturated polyester resins. The wax is pre-dispersed in the resin and during the curing process, the wax forms a thin film on the laminates prepared. The film of wax act as a barrier preventing styrene from evaporating at the moment of curing the laminates. A disadvantage on using waxes is that the wax separates from the resin when the resin mixture is exposed to cold temperatures, becoming inefficient at the time of curing the composite systems.

U.S. Pat. Nos. 5,393,830, 5,492,668, and 5,501,830 propose laminating resins which employs a reduce amount of styrene so as to meet a specified volatile emission level according to test standards. The disclosed resin mixtures include a polyester resin, ethylene glycol dimethacrylate, vinyl toluene, cyclohexyl methacrylate, and bisphenol dimethacrylate. The compositions require high cost diluents and have more difficulty in wetting fibers.

U.S. Pat. No. 6,468,662 describes using a low molecular weight epoxy acrylate in combination with reduce amount of styrene and methacrylate monomers. Glass fiber wetting is improved but cost may be compromised in certain applications.

U.S. Pat. Nos. 5,118,783 and 6,107,446 and U.S. Patent Publication No. 2004/068088, describe the preparation of unsaturated polyesters with low molecular weight. As stated above, resins with low molecular weight and low styrene content may compromise physical properties of the resulting cured materials.

Other approaches to control the molecular weight and add reactivity to the molecules are by end-capping the polymers with unsaturated monomers. U.S. Pat. Nos. 5,096,938 and 6,150,458 describe end-capping of polyester polyols with (meth)acrylic acid or their alkyl esters. A different approach is proposed in U.S. Pat. Nos. 5,373,058 and 5,747,607, where glycidyl methacrylate is used to react with polyesters containing acid end groups.

U.S. Patent Publication Nos. 2004/00776830 and 2007/0179250 propose the preparation of low molecular weight saturated polyester polyols end-capped with at least one (meth)acrylic acid. The esterification process requires a large amount of inhibitors and air during the process which leads to dark products. To obtain good physical properties, the (meth)acrylate intermediates are mixed with styrene.

U.S. Pat. No. 6,153,788 describes the preparation of monohydric and polyhydric alcohols and polyesters reacted with (metha)acrylate end groups. The esterification is carried in the presence of an esterification catalyst, phenolic inhibitors, a solvent to help azeotropically remove the water generated, air is passed though the reaction medium, and a monofunctional epoxy to neutralize the mixture. High viscosities are reported for the polyester acrylate intermediate is reported.

U.S. Pat. No. 6,458,991 proposes the preparation of hydroxyl containing polyfunctional intermediates esterified with acrylic or methacrylic acid in the presence of esterification catalyst, hypophosphorus acid, a Cupper salt, a solvent and an air flow passed through the mixture. Acid neutralization is done using calcium oxide and sodium sulfide. Problems are encountered with the process removing completely the calcium oxide and having residual sodium sulfide which prevents crosslinking of the acrylate intermediate under room temperature curing conditions.

U.S. Pat. Nos. 6,063,957, 6,150,458, and 5,821,383 describe hydroxyl containing polyfunctional alcohols and polyesters, esterified acrylic acid, an esterification catalyst, a solvent, peholic inhibitors, antioxidants and in the presence of air. Amines are used to scavenge the catalyst and residual acid. It is common to observe that amines in the presence of air and temperature oxidize thereby increasing the color of the mixtures.

U.S. Pat. No. 6,268,467 describes unsaturated polyester resins for gelcoat applications having a number average molecular weight of 700-2500 and a weight average of 2600 to 6000. The resins are dissolved in a styrene content ranging from 28 to 35%. The low styrene content is added to minimize the problem with volatile organic emissions (VOC).

U.S. Patent Publication No. 2009/0022998 describes unsaturated polyester for gelcoat applications containing styrene in a concentration as low as 28%. The low styrene content is added to control the VOC emissions.

U.S. Patent Publication No. 2009/076218 describes unsaturated polyesters for gelcoat applications end-capped with glycidyl methacrylate having a number average molecular weight from about 500 to 2500. The references propose that if the molecular weight is less than 560, the curing and gelcoat properties will be poor. In addition, if the molecular weight is higher than about 2500, the resulting resin will have a high viscosity and can not be used to make a low VOC gelcoat. The reference proposes styrene content of up to 30% in combination with 30 percent 1,6-hexanediol diacrylate.

There; however, remains a need in the art to address the various problems noted above in producing vinyl-containing compounds. Specifically, it would be advantageous to minimize the color of the resulting materials, obtain products with high reactivity that can undergo crosslinking at room temperature and also provide a process that does not require the extra steps often required in forming vinyl-containing compounds such as, for example, extraction, separation, filtration and/or washing. Such a process could advantageously be employed in the preparation of gelcoats, and applied in a number of other applications such as, for example, sheet molding compounding (SMC) resins, castings resins, UV cured resins and adhesives, pultrusion resins, corrosion resistant resins, flame retardant resins, low or zero styrene content resins, filament winding, hand lay-up, resin transfer molding, prepregs, coating resins and the like.

SUMMARY OF THE INVENTION

The present invention provides a process for forming vinyl-containing compounds. Such a process eliminates the need for the multiple steps of the prior art processes and provides vinyl-containing compounds with low color. Such a resin system is substantially free of hazardous air pollutants and/or have a minimum amount of reactive solvent such as styrene or polyfunctional (meth)acrylates.

In an example embodiment, the present invention provides a process for preparing vinyl-containing compounds used, for example, in gelcoats having a low molecular weight, low viscosity and reactive groups within the molecule.

The process for forming vinyl-containing compounds comprises the steps of: a) reacting in a nitrogen atmosphere a dicarboxylic acid and/or anhydride and a functional mono or polyfunctional alcohol to provide a hydroxyl-containing polyester; b) reacting the hydroxyl-containing polyester with a vinyl-containing organic acid in the presence of an esterification catalyst, a polymerization inhibitor and an azeotropic agent; and c) reacting the vinyl functional esterified intermediate, residual esterification catalyst and residual vinyl-containing organic acid with an epoxy to provide the vinyl-containing compound.

DETAILED DESCRIPTION OF PREFERRED EMBODIMENTS

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

The term "consists essentially of" (and grammatical variants), as applied to the methods in this invention, means the methods or compositions can contain additional steps as long as the additional steps or components do not materially alter the basic and novel characteristic(s) of the present invention.

The term "consisting of" excludes any additional step that is not specified in the claim.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

All patents, patent applications and publications referred to herein are incorporated by reference in their entirety. In case of a conflict in terminology, the present specification is controlling.

As one of ordinary skill in the art may appreciate, the parameters described herein may vary greatly depending on the process, formulation and/or apparatus as well as the desired properties of the final product.

In one aspect, the invention relates to a process for preparing vinyl-containing components. The process as described above includes reacting in or under a nitrogen atmosphere, a dicarboxylic acid and/or anhydride, and a polyhydric alcohol to provide a hydroxyl-containing polyester. The hydroxyl-containing polyester is reacted with a vinyl-containing organic acid in the presence of an esterification catalyst, a polymerization inhibitor and an azeotropic agent. The reaction then continued using a residual esterification catalyst and residual vinyl-containing organic acid and reacting with an epoxy to provide the vinyl-containing compound.

In accordance with embodiments of the present invention, hydrogen-containing polyesters, typically having a low molecular weight, are prepared by the condensation of dicarboxylic acid or anhydrides with polyhydric alcohols under a nitrogen atmosphere. Anhydrides that can be employed in the making of a polyester are preferably cyclic or acyclic, saturated or unsaturated. In a "cyclic" anhydride, the anhydride functionality is contained within a ring, such as in phthalic anhydride and maleic anhydride. "Saturated" anhydrides contain no ethylenic unsaturation, although they may contain aromatic rings. Phthalic anhydride and succinic anhydride are examples of saturated anhydrides. "Unsaturated" anhydrides contain ethylenic unsaturation. This unsaturation typically becomes incorporated into the polyetherester, and can be used for crosslinking. Examples include maleic anhydride, itaconic anhydride, and the like.

Specific examples of suitable anhydrides include, but are not limited to, propionic anhydride, maleic anhydride, phthalic anhydride, tetrabromophthalic anhydride, succinic anhydride, tetrahydrophthalic anhydride, hexahydrophthalic anhydride, citraconic anhydride, itaconic anhydride, and aryl-, alkyl-, and halogen-substituted derivatives of the above. Mixtures of these anhydrides may be used. The selection of the amounts of polyether and anhydride that may be used can be determined by one skilled in the art depending on end use, and may depend, for example, upon the types of physical properties or degree of crosslinking that is desired for such use.

Specific examples of dicarboxylic acids include but are not limited to, isophthalic acid, terephthalic acid, adipic acid, cyclohexane dicarboxylic acid, succinic anhydride, adipic acid, sebacic acid, azealic acid, malonic acid, alkenyl succinic acids such as n-dodecenylsuccinic acid, docecylsuccinic acid, octadecenylsuccinic acid, and anhydrides thereof. Lower alkyl esters of any of the above may also be employed. Mixtures of any of the above are suitable.

Additionally, polybasic acids or anhydrides thereof having not less than three carboxylic acid groups may be employed. Such compounds include 1,2,4-benzenetricarboxylic acid, 1,3,5-benzene tricarboxylic acid, 1,2,4-cyclohexane tricarboxylic acid, 2,5,7-naphthalene tricarboxylic acid, 1,2,4-naphthalene tricarboxylic acid, 1,3,4-butane tricarboxylic acid, 1,2,5-hexane tricarboxylic acid, 1,3-dicarboxyl-2-methyl-2-carboxymethylpropane, tetra(carboxymethyl) methane, 1,2,7,8-octane tetracarboxylic acid, and mixtures thereof.

A wide range of alcohols may be used in the method of the invention, the selection of which can be determined by one skilled in the art. Examples include monofunctional alcohols and polyfunctional alcohols. It is preferred that these alcohols have sufficiently high boiling points such that themselves and their corresponding esters formed therefrom are not volatilized and lost under the reaction condition. As an example, monoalcohols or polyols containing two or more carbons and alcohols containing at least one or more hydroxy groups having sufficiently high boiling points may be used in the invention. The alcohols may include, but are not limited to, n-butanol, n-hexanol, octanol, undecanol, dodecanol, cyclohexylmethanol, benzyl alcohol, phenoxy ethanol, ethylene glycol, diethylene glycol, neopentyl glycol, dibromoneopentyldiol, polytetramethylene glycol, 1,5-pentanediol, 1,4-butanediol, 2-methyl propanediol, 2,2,4-trimethyl-1,3pentadiol, 2-butyl-2ethyl-1,3-propanediol, ethoxylated hydrogenated bisphenol "A", 1,4-cyclohexane dimenthanol, sorbitol, 1,2,3,6-hexatetrol, 1,4-sorbitol, pentaerythritol, dipentaerythritol, tripentaerythritol, sucrose, 1,2,4-butanetriol, 1,2,5-pentanetriol, glycerol, 2-methyl propanetriol, 2-methyl-1,2,4-butanetriol, trimethylol ethane, trimethylol propane, 1,3,5-trihydroxyethyl benzene, poly-THF, polyethyleneoxide, and polypropyleneoxide. Hydroxyalkyl phenols may also be used and they may be contained as hydroxyethyl, hydroxypropyl, or hydroxybutyl, where the degree of ethoxylation or propoxylation may be from 1 to 20 repeating units. Examples of some useful polyhydric phenols, which are hydroxyalkoxylated, include, catechol, resorcinol, bisphenol intermediates, and the like. Other alkyl or aryl alcohols may be included along with mixtures of any of the above.

The resulting hydroxyl-containing polyester is reacted with a vinyl-containing organic acid in the presence of an esterification catalyst, a polymerization inhibitor and an azeotropic agent to provide an esterified intermediate. An azeotropic agent is present to facilitate removal of water generated during this reaction. The organic acid is present in a molar excess relative to the alcohol and carrying the reaction under nitrogen inert conditions until neutralized. During this reaction, the esterified intermediate and/or the azeotropic agent may serve as a reaction diluent. The reaction between the epoxy, the unreacted organic acid, and the excess esterification catalyst forms a vinyl-containing compound. Preferably, the unreacted organic acid and excess esterification acid catalyst are completely consumed by the process of the invention.

The organic acid that may be used in accordance with the invention may be selected from any number of acids that are used in esterification reactions. Typically, acids having at least two or more carbon and oxygen atoms may be used. Examples of these acids include, but are not limited to, halogenated acrylic or methacrylic acids, cinnamic acid, and crotonic acid, as well as mixtures of the above. Hydroxyalkyl acrylate or methacrylate half esters of dicarboxylic acids as described can also be utilized, and particularly those having from two to six carbon atoms. Examples of these compounds are described in U.S. Pat. No. 3,367,992, the disclosure of which is incorporated herein by reference in its entirety. The organic acid and alcohol may be selected in various amounts relative to one another. Preferably, these materials are used such that the weight equivalent ratio of organic acid to alcohol ranges from about 1:1 to about 10:1.

Any number of esterification acid catalysts can be used for the purposes of the invention. Acid catalysts include, but are not limited to, strong protic acids and Lewis acids. Examples of Lewis acids are sulfuric acid, hydrochloric acid, alkyl sulfonic acids, 2-methyl-1-phenol-4-sulfonic acid, alkylbenzene sulfonic acids, and mixtures thereof. Toluenesulfonic acid, benzenesulfonic acid, xylenesulfonic acid, and methanesulfonic acid are preferably employed. In general, sulfur-containing acid catalysts are preferably employed. Mixtures of any of the above may also be used.

Various amounts of catalyst may be employed. Preferably, the catalyst ranges from about 0.1 to about 5 percent based on the weight of the reactants, and more preferably from about 0.5 to about 2 percent by weight.

Polymerization inhibitors may also be included in the polymerization mixture such as triphenyl antimony, phenothiazine, phenol, 2,6-di-tert-butyl-4-methyl phenol, hydroquinone (HQ), tolu-hydroquinone (THQ), bisphenol A (BPA), naphthoquinone (NQ), p-benzoquinone (p-BQ), butylated hydroxy toluene (BHT), Hydroquinone monomethyl ether (HQMME), 4-ethoxyphenol, 4-propoxyphenol, and propyl isomers thereof, monotertiary butyl hydroquinone (MTBHQ), ditertiary butyl hydroquinone (DTBHQ), tertiary butyl catechol (TBC), 1,2-dihydroxybenzene, 2,5-dichlorohydroquinone, 2-acetylhydroquinone, 1,4-dimercaptobenzene, 2,3,5-trimethylhydroquinone, 2-aminophenol, 2-N,N,-dimethylaminophenol, catechol, 2,3-dihydroxyacetrophenone, pyrogallol, 2-methylthiophenol. Other substituted and un-substituted phenols and mixtures of the above.

As recited, an azeotropic agent is employ to facilitate removal of water generated during the reaction between the organic acid and the alcohol. Preferably, an inert organic azeotropic agent is used. Examples of the azeotropic agent include, but are not limited to, hydrocarbons such as benzene, toluene, xylene, hexane, and cyclohexane. Mixtures of these solvents may also be used. In general, it is preferable to employ solvents having a boiling point ranging from about 70° C. to about 150° C.

The azeotropic agent may be used in varying amounts. In one embodiment, the azeotropic agent is used in an amount ranging from about 5 to about 50 percent based on the weight of the total reaction mixture. Alternatively, the azeotropic agent is used in an amount ranging from about 10 to about 30 percent by weight.

The esterification is carried out under nitrogen and at atmospheric, subatmospheric or reduced pressure, the selection of which is within the skill of one in the art.

Any number of epoxies can be used for the purposes of the invention. Typically, polyepoxides are used. Preferably the polyepoxides are glycicyl methacrylate, glycidyl polyethers of both polyhydric alcohols and polyhydric phenols, flame retardant epoxy resins based on tetrabromo bisphenol A, epoxy novolacs, epoxidized fatty acids or drying oil acids, epoxidized diolefins, epoxidized unsaturated acid esters as well as epoxidized unsaturated polyesters. Mixtures of the above may be employed. The polyepoxides may be monomeric or polymeric. In one embodiment, the polyepoxides are glycidyl ethers of polyhydric alcohols or polyhydric phenols having equivalent weights per epoxide groups ranging from about 150 to about 1500, alternatively from about 150 to about 1000.

The epoxy component can be used in varying amounts. As an example, an epoxy may be reacted with an acid in a proportion of about 1 equivalent of epoxy per each equivalent of acid. The term "acid" in the preceding sentence encompasses excess esterification catalyst and unreacted organic acid. In one embodiment, the proportions of equivalents may range from about 0.8:1 to about 1.2:1. Upon completion of the reaction between the organic acid and the alcohol, the resulting reaction mixture typically contains ester-containing products, unreacted organic acid, an esterification acid catalyst, and azeotropic agent. The reactor is then charged with the epoxy, to react with the excess organic acid and catalyst. In the event that an epoxide is employed, a second esterification catalyst may be used to catalyze the reactions between the epoxide and: (1) unreacted organic acid and (2) esterification acid catalyst. A number of catalysts may be employed for this purpose. Exemplary second esterification catalysts include, but are not limited to, organophosphonium salts, and tertiary amines such as 2,4,6-tri(dimethylaminomethyl)phenol and the like. Tertiary amines and quaternary ammonium salts may be used. Examples include, but are not limited to, tetramethylammonium chloride, tetramethylammonium hydroxide, tetramethylammonium bromide, tetramethylammonium hydrogensulfate, benzyltrimethylammonium chloride, benzyltrimethylammonium bromide, benzyltrimethylammonium hydrogen sulfate, benzyltributylammonium chloride, benzyltributylammonium bromide, benzyltributylammonium hydrogen sulfate, 1,4-diazabicyclo[2.2.2]octane, diazabicyclo[4.3.0]-nonene-(5), 2-methyl imidazol, piperidine, morpholine, triethyl amine, tributyl amine, and the like. Mixtures of the above may also be employed.

Phosphorous containing compounds may also be used as a catalyst involving the epoxide. Examples include, but are not limited to, and may have the formula:

$(R_4)_3P$ or $(R_4)_4PY$ where $R_4$ is an aliphatic, cycloaliphatic or aromatic group containing from $C_4$ to $C_{20}$, and may be linear or branched, wherein Y is a group selected from chlorine, bromine, fluorine, iodine, acetate or bicarbonate.

The mixtures formed as a result of the invention can also be combined with materials that are well known to one skilled in the art. Examples of these materials include, for example, waxes, fillers, low shrinking agents, and pigments. Reinforcements can also be used such as, for example, glass fiber and carbon fiber. Accelerators that are known in the art can be used in the processing of the resins and include, for example, peroxides and promoters to form a molded or shaped article.

In the event that the composition is used as a gelcoat and employs an ethylenically unsaturated monomer such as, for example, a vinyl monomer, the laminating resin often comprises less than about 15 percent by weight of such monomer. Employing less than 15 percent by weight of such a monomer may be potentially advantageous from an environmental standpoint relative to conventional resins. As known, the potential risk of any monomer often depends on various processing conditions relating to, for example, temperature, pressure, and monomer concentration. As an example, OSHA has suggested an allowable eight hours time weight average styrene exposure level of 50 ppm. Ethylenically unsaturated monomers that may be included as a diluent, reactant, co-reactant or may be post added once the polymerization of the desired polymer and/or oligomer was completed, and may include those such as, for example, styrene and styrene derivatives such as α-methyl styrene, p-methyl styrene, divinyl benzene, divinyl toluene, ethyl styrene, vinyl toluene, tert-butyl styrene, monochloro styrenes, dichloro styrenes, vinyl benzyl chloride, fluorostyrenes, tribromostyrenes, tetrabromostyrenes, and alkoxystyrenes (e.g., paramethoxy styrene). Other monomers which may be used include, 2-vinyl pyridine, 6-vinyl pyridine, 2-vinyl pyrrole, 2-vinyl pyrrole, 5-vinyl pyrrole, 2-vinyl oxazole, 5-vinyl oxazole, 2-vinyl thiazole, 5-vinyl thiazole, 2-vinyl imidazole, 5-vinyl imidazole, 3-vinyl pyrazole, 5-vinyl pyrazole, 3-vinyl pyridazine, 6-vinyl pyridazine, 3-vinyl isoxozole, 3-vinyl isothiazole, 2-vinyl pyrimidine, 4-vinyl pyrimidine, 6-vinyl pyrimidine, any vinyl pyrazine. Classes of other vinyl monomers also include, but are not limited to, (meth)acrylates, vinyl aromatic monomers, vinyl halides and vinyl esters of carboxylic acids. As is used herein and in the claims, by "(meth)acrylate and the like terms is meant both (meth)acrylates and acrylates. Examples include but are not limited to oxyranyl (meth)acrylates like 2,3-epoxybutyl (meth)acrylate, 3,4-epoxybutyl (meth)acrylate, 10,11 epoxyundecyl (meth)acrylate, 2,3-epoxycyclohexyl (meth)acrylate, glycidyl (meth)acrylate, hydroxyalkyl (meth) acrylates like 3-hydroxypropyl (meth)acrylate, 2-hydroxyethyl (meth)acrylate, 2,5-dimethyl-1,6-hexanediol (meth)acrylate, 1,10-decanediol (meth)acrylate, aminoalkyl (meth)acrylates like N-(3-dimethylaminopentyl (meth)acrylate, 3-dibutylaminohexadecyl (meth)acrylate; (meth)acrylic acid, nitriles of (meth)acrylic acid and other nitrogen containing (meth) acrylates like N-((meth)acryloyloxyethyl)diisobutylketimine, N-((meth)acryloylethoxyethyl)dihexadecylketimine, (meth)acryloylamidoacetonitrile, 2-(meth) acryloxyethylmethylcyanamide, cyanoethyl (meth)acrylate, aryl (meth)acrylates like benzyl (meth)acrylate or phenyl (meth)acrylate, where the acryl residue in each case can be unsubstitute or substituted up to four times; carbonyl-containing (meth)acrylates like 2-carboxyethyl (meth)acrylate, carboxymethyl (meth)acrylate, oxazolidinylethyl (meth) acrylate, N-((meth)acryloyloxy) formamide, acetonyl (meth)acrylate, N-(meth)acryloylmorpholine, N-(meth) acryloyl-2-pyrrolidinone, N-(2-(meth)acryloxyoxyethyl)-2-pyrrolidinone, N-(3-(meth)acryloyloxypropyl)-2-pyrrolidinone, N-(2-(meth)ylacryloyloxypentadecenyl)-2-pyrrolidinone, N-(3-(meth)acryloyloxyheptadecenyl)-2-pyrrolidinone; (meth)acrylates of ether alcohols like tetrahydrofurfuryl (meth)acrylate, vinyloxyethoxyethyl (meth)acrylate, methoxyethoxyethyl (meth)acrylate, 1-butoxypropyl (meth)acrylate, 1-methyl-(2-vinyloxy)ethyl (meth)acrylate, cyclohexyloxymethyl (meth)acrylate, methoxymethoxyethyl (meth)acrylate, bezyloxymethyl (meth)acrylate, furfuryl (meth)acrylate, 2-butoxyethyl (meth)acrylate, 2-ethoxyethoxymethyl (meth)acrylate, 2-ethoxyethyl (meth)acrylate, allyloxymethyl (meth)acrylate, 1-ethoxybutyl (meth)acrylate, ethoxymethyl(meth) acrylate; (meth)acrylates of halogenated alcohols, like 2,3-dibromopropyl (meth)acrylate, 4-bromophenyl (meth) acrylate 1,3-dichloro-2-propyl (meth)acrylate, 2-bromoethyl (meth)acrylate, 2-iodoethyl (meth)acrylate, chloromethyl (meth)acrylate; phosphorus-, boron-, and/or silicon-containing (meth)acrylates like 2-(dimethylphosphato)propyl (meth)acrylate, 2-(ethylphosphito)propyl (meth)acrylate, dimethylphosphinoethyl (meth)acrylate, dimethylphosphinomethyl (meth)acrylate, dimethylphosphonoethyl (meth) acrylate, dimethy(meth)acryloyl phosphonate, dipropyl (meth)acryloyl phosphate, 2-(dibutylphosphono)ethyl methacrylate, 2,3-butelene(meth)acryloylethyl borate, methyldiethoxy(meth)acryloylethoxysilane, diethylphospahtoethyl (meth)acrylate;sulfur-containing (meth) acrylates like ethylsulfinylethyl (meth)acrylate, 4-thiocyanatobutyl (meth)acrylate, ethylsulfonylethyl (meth)acrylate, thiocyanathomethyl (meth)acrylate, methylsulfonylmethyl (meth)acrylate, bis((meth)acryloyloxyethyl) sulfide.

The gelcoat composition may include an agent such as an organic peroxide compound to facilitate curing of the composition. Exemplary organic peroxides may be used and include, for example, cumene hydroperoxide, methyl ethyl ketone peroxide, benzoyl peroxide, acetyl acetone peroxide, 2,5-dimethylhexane-2,5-dihydroperoxide, tert-butyl peroxybenzoate, di-tert-butyl perphthalate, dicumylperoxide, 2,5-dimethyl-2,5-bis(tert-butylperoxy)hexane, 2,5-dimethyl-2, 5-bis (tert-butylperoxy) hexyne 3, bis (tert-butylperoxyisopropyl) benzene di-tert-butyl peroxide, 1,1-di (tert-amylperoxy)-cyclohexane, 1,1-di-(tert-butylperoxy)-3, 3,5-trymethylcyclohexane, 1,1-di-(tert-butylperoxy)-cyclohexane, 2,2-di-(tert-butylperoxy)-butane, n-butyl 4,4-di-(tert-butylperoxy)-valerate, ethyl 3,3-di-(tert-amylperoxy)-butyrate, ethyl 3,3-di-(tert-butylperoxy)-butyrate and the like. Mixtures of any of the above may be used. The agent is preferably employed in an amount from about 1 to 5 percent based on the weight of the laminating resin, more preferably from about 1 to 3 percent by weight, and most preferably from about 1 to 2 percent by weight.

Suitable curing accelerators or promoters may also be used and include, for example, cobalt naphthanate, cobalt octoate, N,N-diethyl aniline, N,N-dimethyl aniline, N,N-dimethyl acetamide, and N,N-dimethyl p-toluidine. Other salts of lithium, potassium, zirconium, calcium and copper. Mixtures of the above may be used. The curing accelerators or promoters in one embodiment are employed in amounts from about 0.005 to about 1.0 percent by weight, sometimes from about 0.1 to 0.5 percent by weight, and often from about 0.1 to 0.3 percent by weight of the resin.

In one embodiment of this invention, the free radical initiator is a photoinitiator, and the gelcoat composition is cured by UV radiation. These include photoinitiators such as benzophenone, acetophenone and its derivatives, benzoin, benzoin ethers, thiozanthones, halogenated compounds, oximes, and acyl phosphine oxides. In one embodiment, the photoinitiators do not discolor when exposed to sunlight, and include, e.g. acyl phosphines oxides and 2-hydroxy-2-methyl-1-phenylpropan-1-one.

Additional additives known by the skilled artisan may be employed in the laminating resin composition of the present invention including, for example, thixotropic agents, pigments, paraffins, fatty acids, fatty acid derivatives, lubricants, antioxideants, air release agents, fillers, and shrink-reducing additives. Various percentages of these additives can be used in the laminating resin composition.

Fillers used in the invention include calcium carbonate of various forms and origins, silica of various forms and origins, silicates, silicon dioxides of various forms and origins, clays of various forms and origins, feldspar, kaolin, zirconia, calcium sulfates, micas, talcs, wood in various forms, glass(milled, platelets, spheres, micro-balloons), plastics (milled, platelets, spheres, micro-balloons), recycled polymer composite particles, metals in various forms, metallic oxides or hydroxides (except those that alter shelf life or viscosity), metal hydrides or metal hydrates, carbon particles or granules, alumina, alumina powder, aramid, bronze, carbon black, carbon fiber, coal (powder), fibrous glass, graphite, molybdenum, nylon, orlon, rayon, silica amorphous, and fluorocarbons.

The resins formed as a result of the processes of the invention can advantageously be employed in a number of other applications such as, for example, sheet molding compounding (SMC) resins, castings resins, UV cured resins and adhesives, pultrusion resins, corrosion resistant resins, flame retardant resins, low or zero styrene content resins, gel coats, filament winding, hand lay-up, resin transfer molding, prepregs, and coating resins.

The invention is highly advantageous relative to prior art processes. For example, the invention allows the preparation of low color (meth)acrylic intermediates, obtain excellent mechanical properties alone or in combination with a reduced level of ethylenically unsaturated vinyl monomer (e.g., styrene) to be employed during the usage of the resin mixture, preferably no more than 10% percent based on the weight of the reactants.

Moreover, since the invention is a relatively simple two step, one pot synthesis, a number of extra processing steps described in the prior art relating to extracting, washing, separating and/or concentrating of various materials can be avoided (i.e., eliminated), particularly washing and separating with aqueous solution to remove excess acid and catalyst. Applicants believe this to be a significant and unexpected advantage of the invention particularly a significant improvement on the preparation of (meth)acrylic intermediates with a low color by using nitrogen.

The present invention will now be described in more detail with reference to the following examples. However, these examples are given for the purpose of illustration and are not to be construed as limiting the scope of the invention.

EXAMPLES

Example 1

1st Stage: In a 3 liter four-neck flask equipped with a thermometer, stainless steel stirrer, nitrogen inlet, and condenser were placed 458 g of Neopentyl glycol (NPG), 466 g of Diethylene glycol (DEG), 688 g of cyclohexane diacid (CHDA). The materials are reacted under a nitrogen sparge at 210° C. until a 1st stage endpoint of an acid number of 10 or less is achieved.

2nd Stage: The reactor is cooled to a temperature of about 100° C. and then 0.48 g (200 ppm) of Phenothiazin, 0.24 g (100 ppm) of triphenyl antimony, 420 g of Toluene, 757 g of Methacrylic acid, and 9 g of Methane sulfonic acid are added to the first stage components above. The temperature is gradually increased to 115° C. and held to azeotropically distill the water from the esterification reaction. After water distillation slow down or stopped, toluene is stripped off from the reaction. Vacuum is applied to completely remove the toluene.

3rd Stage: Temperature is reduced to 90° C. and 95 g of liquid epoxy is added. Temperature is maintained between 90-100° C. and held for one hour. The reactor is cooled to 40° C., the product is filtrated and transfer to storage. The obtained resin was clear liquid and had acid value of 17.8 mg/g, AHPA color of 40 and viscosity of 260 cps. The resin was identified as resin "1" in table 1.

Examples 2-11

The vinyl-containing compounds in Examples 2-11 were prepared using the similar method described in Example 1, except that the reactants molar ratios in the first stage reaction were varied. The molar ratios of the compositions for the vinyl-containing compounds in Examples 1-11 are summarized in Table 1.

TABLE 1

| Resin# | ISO | THPA | HHPA | CHDA | AA | DDSA | NPG | DEG | TEG | MPDiol |
|---|---|---|---|---|---|---|---|---|---|---|
| 1 | | | | 100 | | | 110 | 110 | | |
| 2 | | | 100 | | | | 109 | 109 | | |
| 3 | | | | | 100 | | 109 | 109 | | |
| 4 | | 100 | | | | | 106 | 106 | | |
| 5 | 100 | | | | | | 106 | 106 | | |
| 6 | 70 | 30 | | | | | 106 | 106 | | |
| 7 | 30 | 40 | | | 30 | | | 218 | | |
| 8 | 100 | | | | | | 106 | | | 106 |
| 9 | | 30 | | | 70 | | | 218 | | |
| 10 | 100 | | | | | | | 131 | 87 | |
| 11 | 60 | | | | 24 | 16 | | 218 | | |

ISO: Isophthalic Acid
THPA: Tetrahydrophthalic Anhydride
HHPA: Hexahydrophthalic Anhydride
CHDA: Cyclohexane Diacid
AA: Adipic Acid
DDSA: Dodecenyl Succinic Anhydride
NPG: Neopentyl Glycol
DEG: Diethylene Glycol
TEG: Triethylene Glycol
MPDiol: 2-Methyl-1,3-Propanediol

Samples Testing

Using the resulting vinyl-containing compounds, the following tests were carried out. The viscosity was measured using a Brookfield LV viscometer, Spindle #2 at 30 RPM and at 25° C. The molecular weights (Mw) were measured by GPC. The room temperature gel time (RTG), total time to Peak (TTP) and peak exotherm (RTP) were measured as follows: To a 100 grams of resin were added: 0.15 g of a 12% Cobalt/0.25 g DMAA/100 g resin, Initiator: 1.25 g MEKP-9 (Syrgis)/100 g resin. The results are summarized in Table 2.

TABLE 2

Resins Properties

| Resin # | AN | Viscosity (cps) | Color | Mw | RTG (min.) | TTP (min.) | Exo. |
|---|---|---|---|---|---|---|---|
| 1 | 17.8 | 260 | AHPA: 40 | 764 | 25.7 | 29.7 | 119° C. |
| 2 | 23.0 | 250 | AHPA: 50 | 583 | 36.7 | 41.2 | 122° C. |
| 3 | 18.9 | 75 | AHPA: 30 | 717 | 25.5 | 30.7 | 137° C. |
| 4 | 23.3 | 265 | Gardner: 3 | 552 | 12.5 | 16.7 | 131° C. |
| 5 | 26.2 | 850 | AHPA: 55 | 738 | 13.3 | 16.8 | 132° C. |
| 6 | 28.2 | 375 | AHPA: 55 | 686 | 8..5 | 11.7 | 137° C. |
| 7 | 21.9 | 310 | Gardner: 4 | 675 | 14.3 | 18.1 | 131° C. |
| 8 | 32.0 | 3300 | Gardner: 3 | 758 | 15.3 | 19.3 | 129° C. |
| 9 | 17.5 | 250 | Gardner: 4 | 729 | 15.0 | 18.8 | 133° C. |
| 10 | 23.0 | 810 | Gardner: 4 | 791 | 6.5 | 9.8 | 131° C. |
| 11 | 20.0 | 480 | Gardner: 4 | 767 | 21.0 | 24.5 | 121° C. |

Examples 12 and 13

The resin of Example 6 was selected to perform room temperature gel tests with different promoters. In addition, styrene was added to observe curing behavior with the reactive monomer. The resin of Example 6 was blended with 5% styrene and is identified as Example 12 in Table 3. The resin of Example 6 was blended with 10% styrene and is identified as Example 13 in Table 3. Data is summarized in Table 3.

TABLE 3

Room Temperature Gel: 100 g resin w/ different Promoters

| Example | Promoter | RTG | TTP | Exo. |
|---|---|---|---|---|
| 6 | 0.15 g 12% cobalt | 48.3 min | 53.6 min | 137° C. |
| 6 | 0.15 g 12% cobalt 0.25 g DMAA | 8.5 min | 11.7 min | 137° C. |
| 6 | 0.15 g 12% cobalt 0.3 g Potassium Octoate | 35 min | 39.5 min | 134° C. |
| 6 | 0.15 g 12% cobalt 0.1 g DMA | 2 min | 5 min | 134° C. |
| 12 | 0.15 g 12% cobalt | 27.5 min | 36.7 min | 141° C. |
| 13 | 0.15 g 12% cobalt | 28.3 min | 41.7 min | 147° C. |

DMAA: N,N-Dimethylacetoacetamide
DMA: N,N-Dimethylaniline

Comparative Examples A-C

A sample with composition similar to the resin of Example 6 was made in an air atmosphere (instead of a nitrogen atmosphere as in Example 6), and is identified as Comparative Example A in Table 4.

Photomer 5429 is a polyester based vinyl compound obtained from Cognis Corp. and is identified as Comparative Example B.

Genomer 3485 is a polyester based vinyl compound, identified as Comparative Example C in Table 4 and available from Rahn Corp.

Table 4 shows that the resin of Example 6 of the present invention has very light color and good cure at room temperature, while the Comparative Example resin A made under an air atmosphere had dark color. Comparative Example resins B and C were not able to cure at room temperature even after 3 weeks under the same curing conditions as the resin of Example 6. This suggests that the Comparative Example resins B and C may contain a large amount of inhibitors or other processing components that prevent premature gelation during the esterification reaction with acrylic intermediates and to keep the color at a relatively low level. However, by increasing the inhibitors or other processing components, curing at room temperature with amine and cobalt salts promoters and peroxides is not possible as shown in Table 4.

TABLE 4

Resins Properties comparison

| Example | AN | Viscosity (cps) | Color | Mw | RTG (min.) | TTP (min.) | Exo. |
|---|---|---|---|---|---|---|---|
| 6 | 28.2 | 375 | AHPA: 55 | 686 | 8..5 | 11.7 | 137° C. |
| A | 16.0 | 600 | Gardner: 9 | 703 | 7.5 | 10.5 | 134° C. |
| B | 18.0 | 420 | Gardner: 1 | 1128 | Not gel or cure after 3 weeks | | |
| C | 5.9 | 532 | Gardner: 2 | 1523 | Not gel or cure after 3 weeks | | |

Comparative Examples D and E

A Bisphenol A conventional epoxy vinyl ester resin, DION VER® 9100, identified as Comparative Example D, and an Isophthalic/NPG based unsaturated polyester resin POLYLITE® 31211-00, identified as Comparative Example E in Table 5 and available from Reichhold Inc. were compared with the resins of Examples 5 and 6 and resins of Comparative Examples B and C. As shown, the resins of the present invention have excellent physical properties compared to Comparative Examples D and E while employing zero or reduced level of styrene. Castings were prepared by adding 1.0% Benzoyl Peroxide (Lupersol A-98) to the resin, follow by overnight curing at 130° F. and postcuring 2 hrs. at 180° F. and 2 hrs. at 250° F.

TABLE 5

Physical Properties of Clear-Cast Resins

| | Example | | | | | |
|---|---|---|---|---|---|---|
| | 5 | 6 | 12 | 13 | D | E |
| Styrene Content (wt %) | 0 | 0 | 5 | 10 | 44 | 35 |
| Barcol Hardness | 39-41 | 42-46 | 46-49 | 48-49 | 35 | 40 |

TABLE 5-continued

Physical Properties of Clear-Cast Resins

| | Example | | | | | |
|---|---|---|---|---|---|---|
| | 5 | 6 | 12 | 13 | D | E |
| HDT (° C.) | 77 | 80 | 73 | 75 | 104 | 103 |
| Tensile Strength (psi) | 12,196 | 12,627 | 12,573 | 12,702 | 11,600 | 11,700 |
| Tensile Modulus (kpsi) | 559 | 577 | 538 | 521 | 460 | 560 |
| % Elongation at Break | 2.7 | 3.0 | 3.4 | 3.7 | 5.2 | 2.9 |
| Flexural Strength (psi) | 24,073 | 23,482 | 22,985 | 22,934 | 23,000 | 18,100 |
| Flexural Modulus (kpsi) | 688 | 665 | 610 | 607 | 500 | 550 |
| Comp Strength (psi) | 22,286 | 20,687 | NA | NA | NA | NA |
| Comp Modulus (kpsi) | 458 | 435 | NA | NA | NA | NA |

The physical properties of glass fiber reinforced laminates of resins of Examples 6, 12, and 13 were listed in Table 6. In this Table, resins of Examples 6, 12 and 13 of the present invention provide excellent physical properties compared to Comparative Example D resin while employing zero or a small amount of styrene. Laminates were prepared by adding to the resin, 0.2% Cobalt (12% conc.), 0.1% dimethyl aniline (DMA) and 1.25% MEKP-900 peroxide (Syrgis). Curing was performed at room temperature followed by postcuring for 2 hrs. at 250° F.

TABLE 6

Physical Properties of Laminates

| | Example | | | |
|---|---|---|---|---|
| | 6 | 12 | 13 | D |
| Styrene Content (Wt %) | 0 | 5 | 10 | 44 |
| Glass Content (Wt %) | 25 | 25 | 25 | 33 |
| Barcol Hardness | 55-65 | 55-63 | 55-62 | NA |
| Tensile Strength (psi) | 19,453 | 18,162 | 19,060 | 18,130 |
| Tensile Modulus (kpsi) | 1,306 | 1,311 | 1,318 | 1,131 |
| % Elongation at Break | 2.6 | 1.8 | 1.9 | 2.1 |
| Flexural Strength (psi) | 43,441 | 25,782 | 25,507 | 29,008 |
| Flexural Modulus (kpsi) | 1,822 | 1,387 | 1.325 | 1,059 |
| Comp Strength (psi) | 23,688 | 18,880 | 20,376 | NA |
| Comp Modulus (kpsi) | 1,194 | 922 | 963 | NA |

Other Physical Test Examples

Physical properties of clear-cast resins of Examples 1-4, 7-9 and 11 are listed in Tables 7 and 8. Tables 7 and 8 show that the properties of the resins of the present invention can covered a wide range physical properties based on the changes in the compositions while employing zero styrene. Castings were prepared by adding 1.0% Benzoyl Peroxide (Lupersol A-98) to the resin, follow by overnight curing at 130° F. and postcuring 2 hrs. at 180° F. and 2 hrs. at 250° F.

TABLE 7

Physical Properties of Clear-Cast Resins 1-4

| | Example | | | |
|---|---|---|---|---|
| | 1 | 2 | 3 | 4 |
| Styrene Content (wt %) | 0 | 0 | 0 | 0 |
| Barcol Hardness | 38-40 | 45-48 | 10-12 | 39-41 |
| HDT (° C.) | 63 | 59 | 43 | 57 |
| Tensile Strength (psi) | 9,717 | 8,963 | 3,856 | 10,956 |

TABLE 7-continued

Physical Properties of Clear-Cast Resins 1-4

| | Example | | | |
|---|---|---|---|---|
| | 1 | 2 | 3 | 4 |
| Tensile Modulus (kpsi) | 387 | 493 | 138 | 507 |
| % Elongation at Break | 3.6 | 2.5 | 10.6 | 4.1 |
| Flexural Strength (psi) | 16,391 | 16,894 | 5,404 | NA |
| Flexural Modulus (kpsi) | 473 | 534 | 134 | NA |

TABLE 8

Physical Properties of Clear-Cast Resins 7-9 and 11

| | Example | | | |
|---|---|---|---|---|
| | 7 | 8 | 9 | 11 |
| Styrene Content (wt %) | 0 | 0 | 0 | 0 |
| Tensile Strength (psi) | 8,598 | 6,702 | 3,997 | 3,425 |
| Tensile Modulus (kpsi) | 380 | 289 | 218 | 103 |
| % Elongation at Break | 6.5 | 8.8 | 6.9 | 24.0 |

Stability Test Examples

Figure 1:
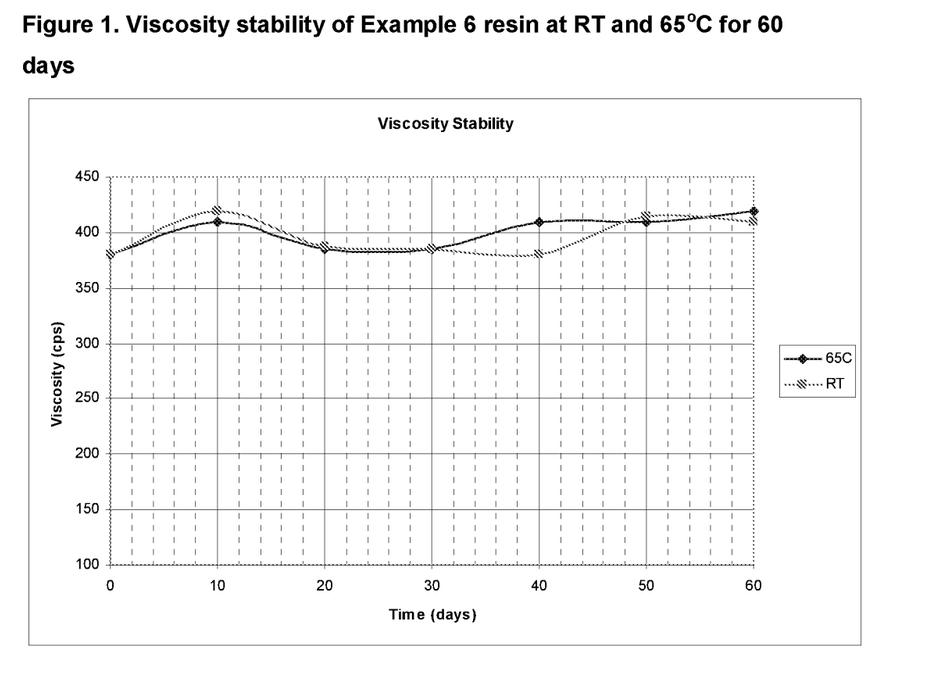
FIG. 1 is a graphic comparison of viscosity versus time at room temperature and at 65° C. for 60 days.
Figure 2:
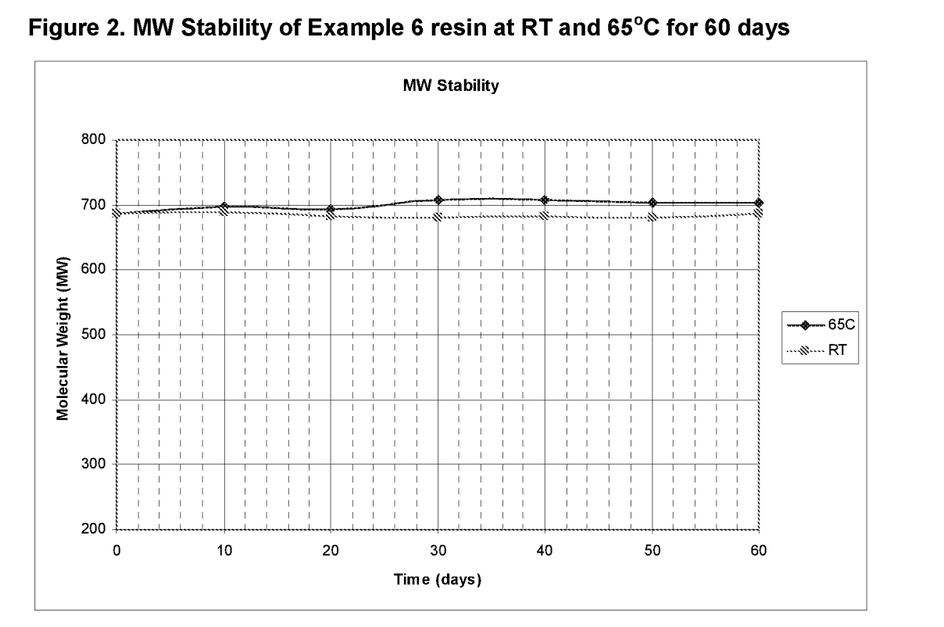
FIG. 2 is a graphic comparison of molecular weight versus time at room temperature and at 65° C. for 60 days.
Figure 3:
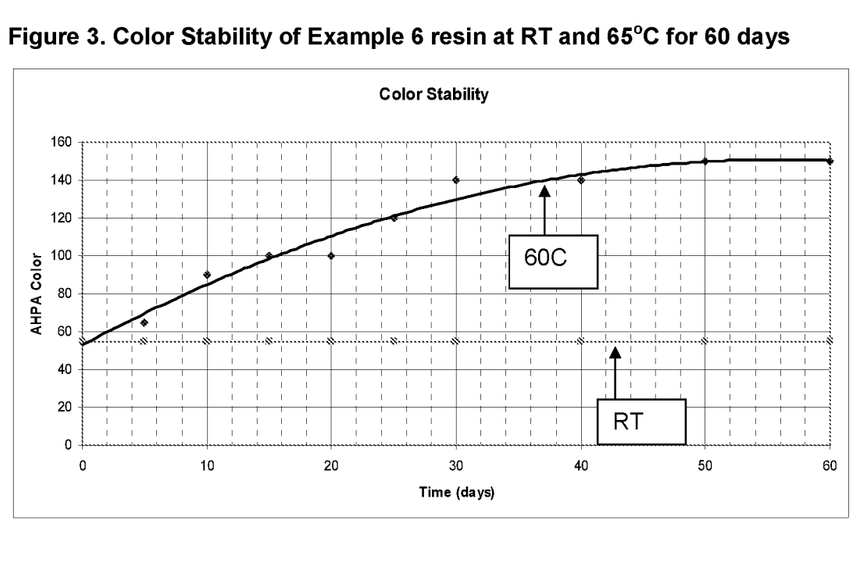
FIG. 3 is a graphic comparison of AHPA color versus time at room temperature and at 65° C. for 60 days.

The Example 6 resin was selected for the stability tests at both room temperature (RT) and 60° C. oven for 60 days. The tests included viscosity, molecular weight (MW), and color. As see from FIGS. 1-3, the Example 6 resin has excellent stability even at 65° C. for up to 60 days.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

The invention claimed is:

1. A process for forming vinyl-containing compounds, the process comprising the steps of:
   a) reacting in a nitrogen atmosphere at least one dicarboxylic acid and/or anhydride and a monofunctional or polyfunctional alcohol to an endpoint of an acid number of 10 or less to provide a hydroxyl-containing polyester;
   b) reacting the hydroxyl-containing polyester with a vinyl-containing organic acid in the presence of an esterification catalyst, and a polymerization inhibitor while in the nitrogen atmosphere to provide a vinyl functional esterified intermediate group; and c) reacting the vinyl functional esterified intermediate, residual esterification catalyst and residual vinyl-containing organic acid with an epoxy while in the nitrogen atmosphere to provide the vinyl-containing compound wherein the nitrogen atmosphere in steps a)-c) is devoid of oxygen and the reactions are under inert conditions.

2. The process according to claim 1, wherein the at least one dicarboxylic acid is selected from the group consisting of isophthalic acid, terephthalic acid, adipic acid, cyclohexane dicarboxylic acid, succinic acid, succinic anhydride, sebacic acid, azealic acid, malonic acid, malonic anhydride, itaconic acid, itaconic anhydride, maleic acid, maleic anhydride, and alkenyl succinic acids, and anhydrides thereof.

3. The process according to claim 2, wherein the anhydride of the dicarboxylic acid is selected from the group consisting of phthalic anhydride, tetrahydrophthalic anhydride, maleic anhydride, itaconic anhydride and hexahydrophthalic anhydride.

4. The process according to claim 1, wherein the alcohol is selected from the group consisting of n-butanol, n-hexanol, octanol, undecanol, dodecanol, cyclohexylmethanol, benzyl alcohol, phenoxy ethanol, ethylene glycol, diethylene glycol, neopentyl glycol, dibromoneopentyldiol, polytetramethylene glycol, 1,5-pentanediol, 1,4-butanediol, 2-methyl propanediol, 2,2,4-trimethyl-1,3pentadiol, 2-butyl-2ethyl-1,3-propanediol, ethoxylated hydrogenated bisphenol "A", 1,4-cyclohexane dimenthanol, sorbitol, 1,2,3,6-hexatetrol, 1,4-sorbitol, pentaerythritol, dipentaerythritol, tripentaerythritol, sucrose, 1,2,4-butanetriol, 1,2,5-pentanetriol, glycerol, 2-methyl propanetriol, 2-methyl-1,2,4-butanetriol, trimethylol ethane, trimethylol propane, 1,3,5-trihydroxyethyl benzene, polyTHF, polyethyleneoxide, and polypropyleneoxide, catechol, resorcinol, and bisphenol intermediates, and mixtures thereof.

5. The process according to claim 1, wherein the vinyl-containing organic acid is selected from the group consisting of methacrylic acid, acrylic acid, cinnamic acid and crotonic acid, and mixtures of any thereof.

6. The process according to claim 1, wherein the epoxy is selected from the group consisting of Bisphenol A epoxy, Bisphenol F epoxy, butyl glycidyl ether, C12-C14 glycidyl ether, cresyl glycidyl ether, glycidyl neodecanoate, diglycidyl ether of neopentyl glycol, diglycidyl ether of 1,4 butanediol, and diglycidyl ether of resorcinol.

7. The process according to claim 1, wherein a second esterification catalyst is added with the epoxy in step (c).

8. The process according to claim 1, wherein the second esterification catalyst is selected from the group consisting of organophosphonium salts and quaternary ammonium salts.

9. A vinyl-containing compound prepared by the process of claim 1 comprising no more than 10% of an ethylenically unsaturated vinyl monomer.

10. A thermosetting resin comprising a vinyl-containing compound prepared by the process of claim 1.

11. The thermosetting resin of claim 10 further includes and initiator comprising one or more organic peroxides and curing accelerators comprising a tertiary amine, an acetoacetamide, and one or more metal salts.

12. The thermosetting resin of claim 10, further comprising an additional additive selected from any one of the group consisting of flame retardant compounds, fillers, reinforcements, thixotropic agents, paraffin waxes, fatty acids, fatty acid derivatives, lubricants, shrink-reducing additives, thermoplastic polymeric materials, low profile agents (LPA), antioxidants, pigments, dyes, paraffins, lubricants, flow agents, air release agents, wetting agents, UV stabilizers, internal release agents, and mixtures of any thereof.

13. A composite component, laminate, structural adhesive, polymer concrete component, or molding component comprising the thermosetting composition according to claim 10.

14. A prepreg comprising the thermosetting composition of claim 10.

15. A coating resin applying the thermosetting composition of claim 10.

16. A method of using a thermosetting composition comprising applying the thermosetting composition of claim 10 by a pultrusion route, casting, hand lay-up, spray-up, filament winding, sheet molding compounding (SMC), UV cured resins, or resin transfer molding.

* * * * *